United States Patent
Park et al.

(10) Patent No.: US 10,029,066 B2
(45) Date of Patent: Jul. 24, 2018

(54) AUDIO APPARATUS AND METHOD FOR INDUCING BRAINWAVE USING BINAURAL BEAT

(71) Applicant: DLOGIXS CO., Ltd, Anyang (KR)

(72) Inventors: Sung-Kee Park, Seongnam (KR); Sang-Ouk Lee, Seoul (KR); In-Taek Jeong, Uiwang (KR); Ju-Mong Kwon, Seoul (KR)

(73) Assignee: DLOGIXS CO., LTD, Anyang (KR)

( * ) Notice: Subject to any disclaimer, the term of this patent is extended or adjusted under 35 U.S.C. 154(b) by 259 days.

(21) Appl. No.: 14/991,249

(22) Filed: Jan. 8, 2016

(65) Prior Publication Data

US 2017/0173296 A1 Jun. 22, 2017

(30) Foreign Application Priority Data

Dec. 16, 2015 (KR) .................. 10-2015-0179732

(51) Int. Cl.
*A61M 21/00* (2006.01)
*A61B 5/024* (2006.01)
*A61B 5/0476* (2006.01)

(52) U.S. Cl.
CPC ............ *A61M 21/00* (2013.01); *A61B 5/024* (2013.01); *A61B 5/0476* (2013.01); *A61M 2021/0027* (2013.01)

(58) Field of Classification Search
CPC .......... A61M 21/00; A61M 2021/0027; A61B 5/024; A61B 5/0476
USPC ............................... 600/26–28; 128/897–899
See application file for complete search history.

(56) References Cited

U.S. PATENT DOCUMENTS

| 2005/0049452 A1* | 3/2005 | Lawlis | A61M 21/00 600/28 |
| 2006/0116600 A1* | 6/2006 | Vesely | A61B 5/04008 600/559 |
| 2007/0084473 A1* | 4/2007 | Hewett | A61M 21/00 128/898 |
| 2007/0282216 A1* | 12/2007 | Vesely | A61B 5/04845 600/545 |

(Continued)

FOREIGN PATENT DOCUMENTS

| JP | H07-132145 A | 5/1995 |
| JP | 2014-507889 A | 3/2014 |

(Continued)

*Primary Examiner* — Navin Natnithithadha
*Assistant Examiner* — Sunita Reddy (57) ABSTRACT

Disclosed herein are an audio apparatus and method for inducing a brainwave using a binaural beat, including a frequency shift unit for receiving a first audio sound source signal and generating a second audio sound source signal by shifting some of the frequency band of the first audio sound source signal by a specific frequency, and an audio output unit connected to the frequency shift unit, for outputting first and second audio output signals corresponding to the first and the second audio sound source signals. Accordingly, a user can hear a music signal or an audio signal for learning without being aware of the distortion of a sound source and can change his or her brainwave state without resistance or monotonousness because a required brainwave state is changed by applying a binaural beat to a specific frequency band of an audio signal, in particular, a music signal.

14 Claims, 7 Drawing Sheets

(56) References Cited

U.S. PATENT DOCUMENTS

| | | | |
|---|---|---|---|
| 2008/0304691 A1* | 12/2008 | Lai | H04R 5/0335 |
| | | | 381/386 |
| 2009/0318826 A1* | 12/2009 | Green | A61B 5/048 |
| | | | 600/545 |
| 2010/0331606 A1* | 12/2010 | Wong | A61M 21/02 |
| | | | 600/27 |
| 2011/0060436 A1* | 3/2011 | Gandini | A61M 21/02 |
| | | | 700/94 |
| 2011/0105938 A1* | 5/2011 | Hardt | A61B 5/0482 |
| | | | 600/544 |
| 2016/0008568 A1* | 1/2016 | Attia | A61M 21/0094 |
| | | | 600/28 |

FOREIGN PATENT DOCUMENTS

| | | | | |
|---|---|---|---|---|
| KR | 10-2008-0001573 A | 1/2008 | | |
| WO | WO 2009139011 A1 * | 11/2009 | | A61M 21/02 |
| WO | WO 2012103940 A1 * | 8/2012 | | A61B 5/0482 |

* cited by examiner

FIG. 1

<PRIOR ART>

FIG. 2

<Frequency spectrum of original sound>

<Frequency spectrum after modulation> binaural beat freq: Target binaural beat freq.

<PRIOR ART>

AUDIO APPARATUS AND METHOD FOR INDUCING BRAINWAVE USING BINAURAL BEAT

CROSS REFERENCE TO RELATED APPLICATION

The present application claims the benefit of Korean Patent Application No. 10-2015-0179732 filed in the Korean Intellectual Property Office on Dec. 16, 2015, the entire contents of which are incorporated herein by reference.

BACKGROUND OF THE INVENTION

1. Technical Field

The present invention relates to an audio apparatus and method for inducing a brainwave using a binaural beat and, more particularly, to an audio apparatus and method for inducing a brainwave using a binaural beat, wherein a music signal or an audio signal for learning can be heard without being aware of the distortion of a sound source and a required brainwave state can be induced without resistance or monotonousness in such a manner that a required brainwave state is induced by applying a binaural beat to a specific frequency band of an audio signal, in particular, a music signal.

2. Description of the Related Art

It has been known that the brain of a person generates a different frequency depending on each state. When a signal of a specific frequency, such a sound or light, continues to be externally applied to the brain, there is an effect in that a brainwave is attuned to the input frequency. In general, mind and body are relaxed when the brain is in a meditation state, and the brain becomes an activation state in the concentration of mind.

Clinical experiments revealed that the brain of a person generates different frequencies during activity, sleeping, and meditation. Such frequencies are commonly called brainwaves. It has been known that the brainwaves include an alpha wave α having a frequency range of 8 Hz~14 Hz, a beta wave β having a frequency range of 15 Hz~24 Hz, a theta wave θ having a frequency range of 4 Hz~8 Hz, and a delta wave δ having a frequency range of 0.4 Hz~4 Hz.

The alpha wave α is chiefly generated when a person is lost in mediation or the mind and body state is comfortable. The beta wave β is chiefly generated when a person is in activity. The theta wave θ is chiefly generated in a deep learning state, a little sleepy state, or a high creativity state. The delta wave δ is chiefly generated when a person in a deep sleeping state or in a coma state.

A binaural beat is a principle in which a required brainwave is induced in the brain using a difference between two frequencies. For example, if a binaural beat sound is 10 Hz, the frequency of 10 Hz resonates the brain, thereby inducing the brainwave 8 Hz~14 Hz of an alpha wave state.

Conventional apparatuses for generating sound sources that induce such brainwaves have been developed, but are problematic in that they have resistance to a sound "hooting" generated when a sound source having a middle and low band frequency of 200 Hz~1 KHz.

In order to solve the problem, another prior art (refer to Patent Document 1) for shifting a frequency of a specific audio signal by a binaural frequency and playing back the audio signal was developed. However, the prior art is problematic in that a user listens to deformed sound quality because all the frequency bands of an audio signal are shifted and thus the user recognizes that a frequency shifts from a low frequency. Furthermore, the prior art has a limit to the efficient induction of a brainwave because the brainwave is induced without taking into consideration the current brainwave state of a user.

PRIOR ART DOCUMENT

Patent Document (Patent Document 1) Patent Document 1: Korean Patent Application Publication No. 10-2008-0001573 (Jan. 3, 2008)

SUMMARY OF THE INVENTION

Accordingly, the present invention has been made keeping in mind the above problems occurring in the prior art, and an object of the present invention is to provide an audio apparatus and method for inducing a brainwave using a binaural beat, wherein a user can hear a music signal or an audio signal for learning without being aware of the distortion of a sound source and can change his or her brainwave state without resistance or monotonousness because a required brainwave state is changed by applying a binaural beat to a specific frequency band of an audio signal, in particular, a music signal.

Another object of the present invention is to provide an audio apparatus and method for inducing a brainwave using a binaural beat, wherein a current brainwave state of a user is changed to a target brainwave state naturally and efficiently because the current brainwave state is taken into consideration and changed to the target brainwave state stepwise.

Technical objects to be achieved by the present invention are not limited to the aforementioned object, and those skilled in the art to which the present invention pertains may evidently understand other technical objects from the following description.

An audio apparatus for inducing a brainwave using a binaural beat in accordance with an embodiment of the present invention includes a frequency shift unit configured to receive a first audio sound source signal and to generate a second audio sound source signal by shifting some of a frequency band of the first audio sound source signal by a specific frequency, an audio output unit connected to the frequency shift unit and configured to output a first audio output signal and a second audio output signal corresponding to the first audio sound source signal and the second audio sound source signal, respectively, and a control unit configured to change at least one of the some frequency band and the specific frequency in response to a user's manipulation or predetermined setting.

An audio apparatus for inducing a brainwave using a binaural beat in accordance with an embodiment of the present invention further includes a mono conversion unit configured to generate the first audio sound source signal from an external audio signal or audio data stored in the audio apparatus as a mono sound source, wherein the mono sound source may include a sound source on one side which is selected from the stereo components of the audio signal or audio data or a sound source generated by mixing the stereo components.

The audio apparatus for inducing a brainwave using a binaural beat in accordance with an embodiment of the present invention may further include an analog-digital converter configured to convert the external audio signal into a digital signal.

In the audio apparatus for inducing a brainwave using a binaural beat in accordance with an embodiment of the present invention, the some frequency band may be selected from a frequency band of 500~6000 Hz, and the specific frequency may include a frequency within any one of the frequency ranges of an alpha wave, beta wave, a theta wave, and delta wave which are brainwaves to be induced.

In the audio apparatus for inducing a brainwave using a binaural beat in accordance with an embodiment of the present invention, the control unit may set a target brainwave state to be induced in response to user setting and determine a brainwave induction sequence so that the target brainwave state is induced.

The audio apparatus for inducing a brainwave using a binaural beat in accordance with an embodiment of the present invention further includes a brainwave sensor attached to the head of the user and configured to detect a current brainwave state and a heartbeat sensor configured to detect the heart rate of the user, wherein the control unit may set a progress sequence so that the target brainwave state is sequentially induced in response to the brainwave state and change playback speed of the first and the second audio sound source signals in response to the heart rate.

In the audio apparatus for inducing a brainwave using a binaural beat in accordance with an embodiment of the present invention, the control unit may control the frequency shift unit so that an induction sequence from the current brainwave state detected by the brainwave sensor to the target brainwave state is sequentially changed from the state in which a frequency of the brainwave is high to the state in which the frequency of the brainwave is low or from the state in which the frequency of the brainwave is low to the state in which the frequency of the brainwave is high.

The audio apparatus for inducing a brainwave using a binaural beat in accordance with an embodiment of the present invention further includes a headphone configured to convert the first and the second audio output signals into sounds and output the sound, wherein the sound corresponding to the first audio output signal may be output to one side of the headphone, and the sound corresponding to the second audio output signal may be output to the other side of the headphone.

A method for inducing a brainwave using a binaural beat in accordance with an embodiment of the present invention includes a frequency shift step for receiving a first audio sound source signal and generating a second audio sound source signal by shifting some of a frequency band of the first audio sound source signal by a specific frequency, an audio output step for outputting a first audio output signal and a second audio output signal corresponding to the first audio sound source signal and the second audio sound source signal, respectively, and a control step for changing at least one of the some frequency band and the specific frequency in response to a user's manipulation or predetermined setting.

The method for inducing a brainwave using a binaural beat in accordance with an embodiment of the present invention further includes a mono sound source conversion step for generating the first audio sound source signal from an external audio signal or audio data stored in a sound source storage unit, wherein the mono sound source may include a sound source on one side which is selected from the stereo components of the audio signal or audio data or a sound source generated by mixing the stereo components.

In the method for inducing a brainwave using a binaural beat in accordance with an embodiment of the present invention, the some frequency band may be selected from a frequency band of 500~6000 Hz, and the specific frequency may include a frequency within any one of the frequency ranges of an alpha wave, beta wave, a theta wave, and delta wave which are brainwaves to be induced.

In the method for inducing a brainwave using a binaural beat in accordance with an embodiment of the present invention, the control step may include a user setting step for setting a target brainwave state to be induced in response to user setting and determining a brainwave induction sequence so that the target brainwave state is induced.

The method for inducing a brainwave using a binaural beat in accordance with an embodiment of the present invention further includes a brainwave sensing step for detecting a brainwave state of the user and a heartbeat sensing step for detecting the heart rate of the user, wherein the control step may include setting a progress sequence so that the target brainwave state is sequentially induced in response to the brainwave state and changing playback speed of the first and the second audio sound source signals in response to the heart rate.

In the method for inducing a brainwave using a binaural beat in accordance with an embodiment of the present invention, the control step may include controlling the frequency shift step so that an induction sequence from a current brainwave state detected in the brainwave sensing step to the target brainwave state is sequentially changed from the state in which a frequency of the brainwave is high to the state in which the frequency of the brainwave is low or from the state in which the frequency of the brainwave is low to the state in which the frequency of the brainwave is high.

DETAILED DESCRIPTION

Hereinafter, embodiments of the present invention are described in detail with reference to the accompanying drawings. The following detailed description is only illustrative and illustrates only some embodiments of the present invention.

Figure 1:
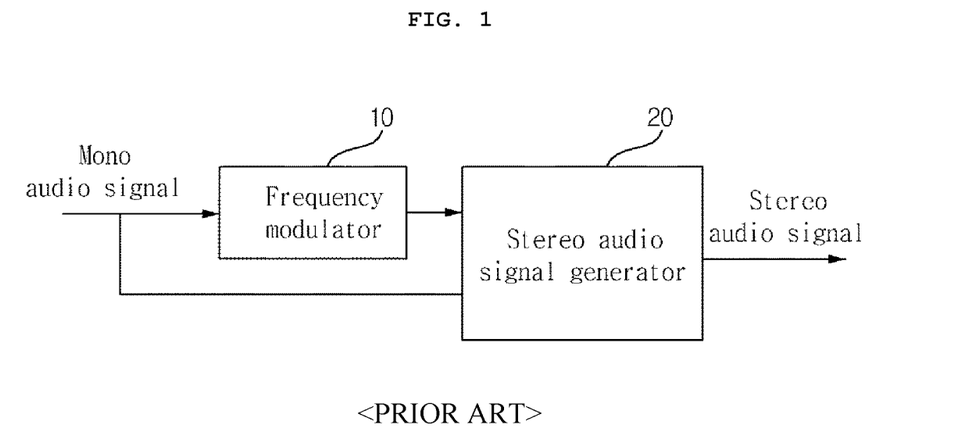
FIG. 1 is a block diagram of a conventional apparatus for inducing a brainwave.
Figure 2:
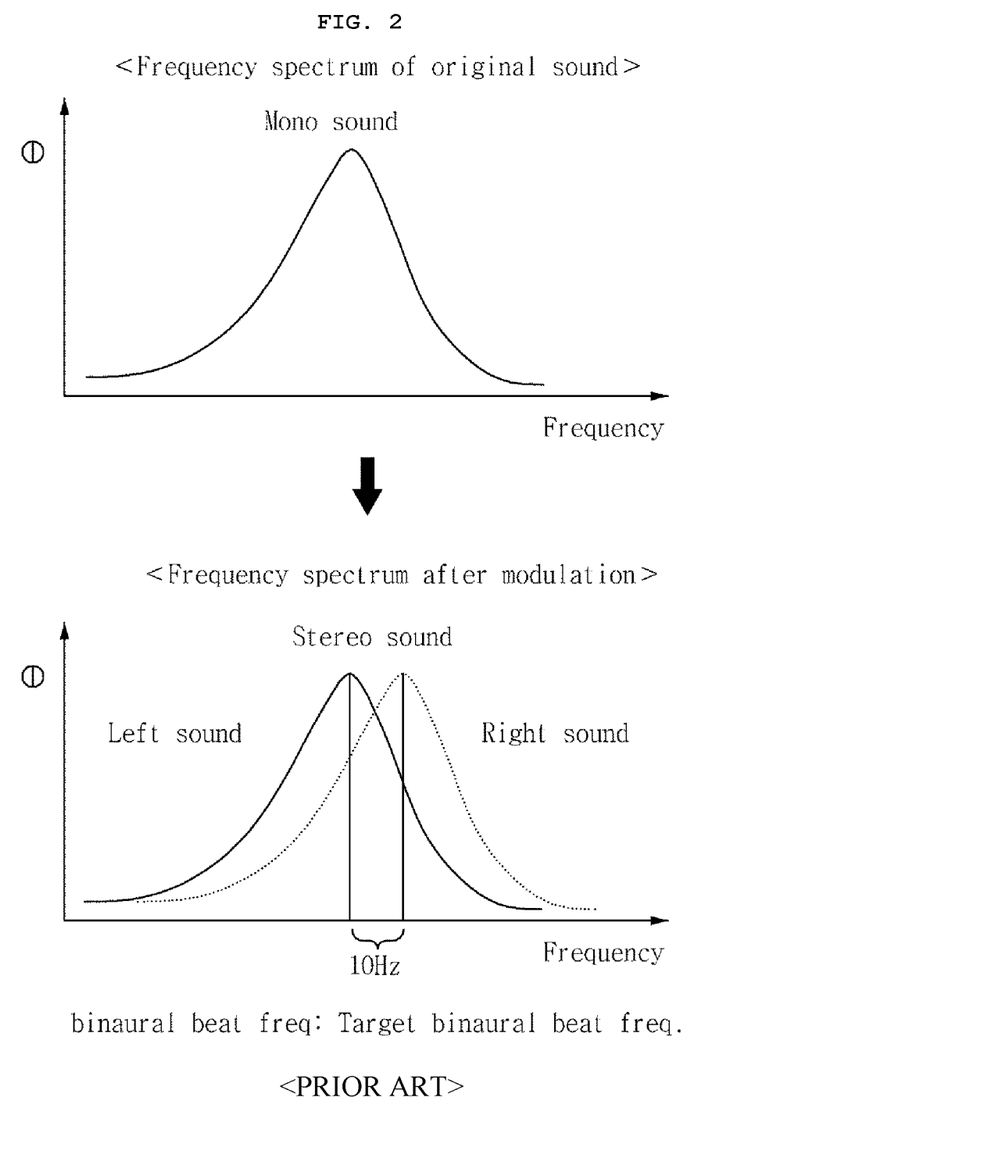
FIG. 2 is a diagram showing frequency spectra according to the conventional apparatus for inducing a brainwave.
Figure 3:
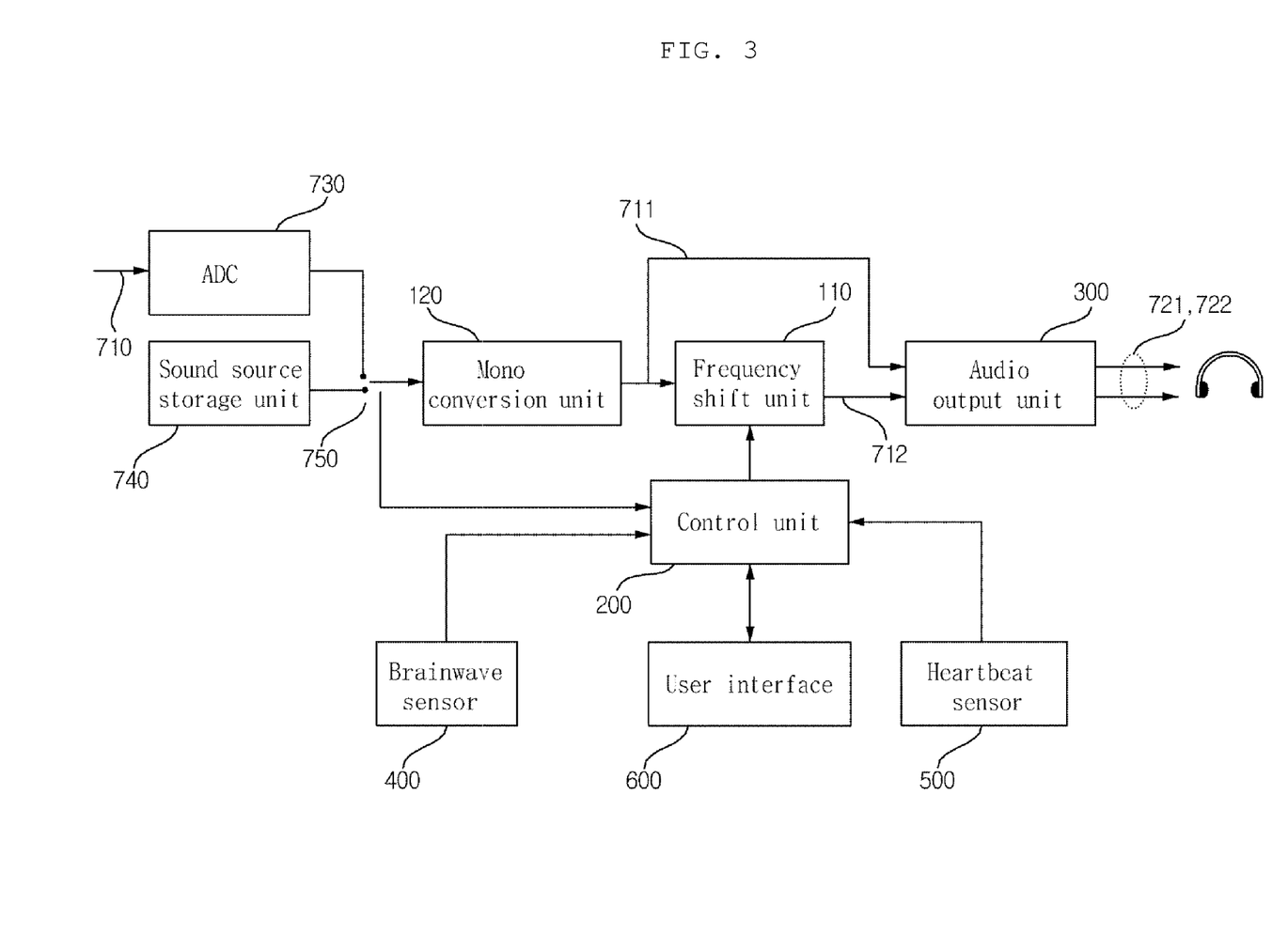
FIG. 3 is a block diagram of an audio apparatus for inducing a brainwave using a binaural beat in accordance with an embodiment of the present invention.

FIG. 3 is a block diagram of an audio apparatus for inducing a brainwave using a binaural beat in accordance with an embodiment of the present invention.

Referring to FIG. 3, the audio apparatus for inducing a brainwave according to an embodiment of the present invention includes a frequency shift unit 110 configured to receive a first audio sound source signal 711 and to generate a second audio sound source signal 712 generated by shifting some of the frequency band of the first audio sound source signal by a specific frequency, an audio output unit 300 connected to the frequency shift unit 110 and configured to output a first audio output signal 721 and a second audio output signal 722 corresponding to the first audio sound source signal 711 and the second audio sound source signal 712, respectively, and a control unit 200 configured to change at least one of the some frequency band and the specific frequency in response to a user's manipulation or predetermined setting.

The first audio sound source signal 711 may be obtained from a signal, selected from an external sound source 710 and sound source data stored in a sound source storage unit 740, through a sound source selection unit 750. If the first audio sound source signal 711 is obtained from the external sound source 710 of an analog form, the audio apparatus may further include an analog-digital converter (ADC) 730 for converting the analog signal into a digital signal. Furthermore, if the external sound source 710 or sound source data stored in the sound source storage unit 740 is a stereo signal, the audio apparatus may further include a mono conversion unit 120 configured to extract a mono sound source and to convert the mono sound source into the first audio sound source signal 711 inputted to the frequency shift unit 110.

The audio apparatus for inducing a brainwave in accordance with an embodiment of the present invention may further include a brainwave sensor 400 attached to the head of a user and configured to detect the brainwave state of the user and a heartbeat sensor 500 configured to detect the heart rate of a user in order to determine a brainwave induction step or an induction sequence in response to the current brainwave or heart beat state of a user.

The frequency shift unit 110 is an element for generating the second audio sound source signal 712 by shifting some of the frequency band of the input first audio sound source signal 711 by a specific frequency and may be implemented using a known digital signal processor (DSP). In this case, it is to be noted that the control unit 200 sets a frequency band and frequency quantity to be shifted in the frequency shift unit 110 by taking into consideration the frequency of a target brainwave and the frequency shift unit 110 shifts a frequency component of the frequency band by the frequency quantity with respect to the first audio sound source signal 711 and outputs the shifted frequency band as the second audio sound source signal 712.

It has been known that in a person's hearing sense, a distinction limit to a change of a frequency of 500~6000 Hz is 0.3%. In other words, in the frequency range of 500~6000 Hz, a change of a frequency of 1.5~18 Hz can be recognized by a person's aural ability. If a frequency is shifted using a binaural beat, when 0.3% or more of the frequency band is shifted, a person recognizes a change of sound quality.

Accordingly, a frequency band to be shifted and a frequency quantity to be shifted are associated with the frequency of a brainwave to be induced. For example, if the alpha wave (8~14 Hz) is to be induced, a frequency quantity that is shifted in order to use a binaural beat is set as a range of 8~14 Hz. Furthermore, the lowest limit of a frequency band shifted so that a user is unable to recognize a change of the sound quality of a sound source even through a frequency shift may be set to 8~14/0.3%, that is, a range of 2667~4667 Hz.

Table 1 shows target brainwaves to be induced and the lowest limits of corresponding shift frequency quantities and shift frequency bands.

TABLE 1

| STATE OF TARGET BRAINWAVE | | | |
|---|---|---|---|
| STATE OF BRAINWAVE | FREQUENCY | FREQUENCY QUANTITY | LOWEST LIMIT OF SHIFT FREQUENCY BAND |
| Delta wave | 0.4~4 Hz | 0.4~4 Hz | 133~1333 Hz |
| Theta wave | 4~8 Hz | 4~8 Hz | 1333~2667 Hz |
| Alpha wave | 8~14 Hz | 8~14 Hz | 2667~4667 Hz |
| Beta wave | 15~24 Hz | 15~24 Hz | 5000~8000 Hz |

If a target brainwave to be induced is set by a user, in order to induce the target brainwave, the control unit 200 sets a frequency band to be shifted and a frequency quantity to be shifted in the frequency components of the first audio sound source signal 711 with reference to the values listed in Table 1. The frequency shift unit 110 generates the second audio sound source signal 712 by shifting the frequency of the first audio sound source signal 711. In this case, the lowest limit of the frequency band to be shifted may be set as a range of a value or more listed in Table 1, the frequency band to be shifted may be set as a band of 500~6000 Hz, and a corresponding frequency quantity may be set.

Figure 5A:
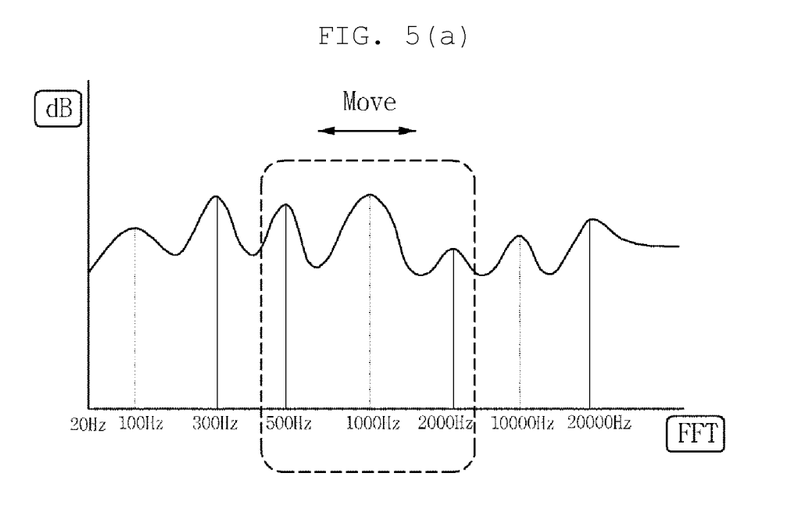
FIGS. 5(a) and 5(b) are conceptual diagrams of a frequency shift according to the audio apparatus for inducing a brainwave according to an embodiment of the present invention.
Figure 5B:
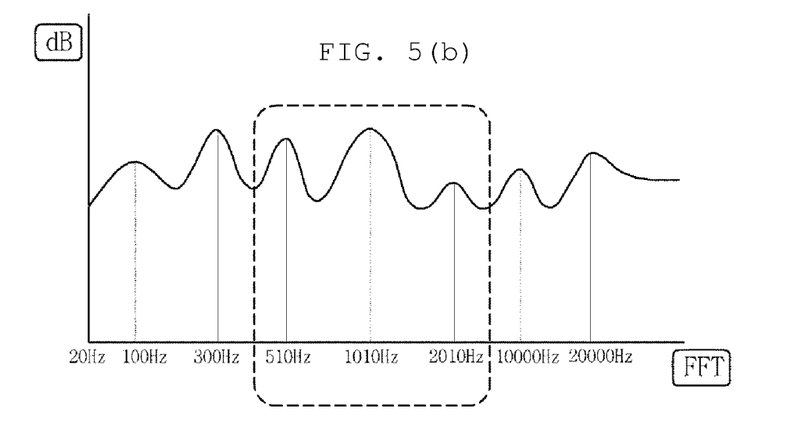

FIGS. 5(*a*) and 5(*b*) are conceptual diagrams of a frequency shift according to the audio apparatus for inducing a brainwave according to an embodiment of the present invention. FIG. 5(*a*) shows the frequency components of the first audio sound source signal 711 prior to the shift of a frequency. FIG. 5(*b*) shows the frequency components of the second audio sound source signal 712 after some of the frequency band of the first audio sound source signal 711 is shifted using the audio apparatus for inducing a brainwave in accordance with an embodiment of the present invention.

In order to induce the alpha wave, if a frequency quantity to be shifted is set to 10 Hz and a frequency band to be shifted is set to 500~2000 Hz, the frequency band of 500~2000 Hz of the first audio sound source signal 711 is shifted 10 Hz by the frequency shift unit 110 as shown in FIG. 5(*b*), thus moving to a frequency band of 510~2010 Hz. In this case, the frequency band to be shifted has been assumed to be 500~2000 Hz. However, referring to Table 1, if the frequency to be shifted is set to 10 Hz as described above in order to induce the alpha wave, the lowest limit of a frequency band to be shifted may be set to 3333 Hz (~10 Hz/0.3%) and a frequency shift may be performed on a band equal to or higher than the frequency band to be shifted.

Figure 4:
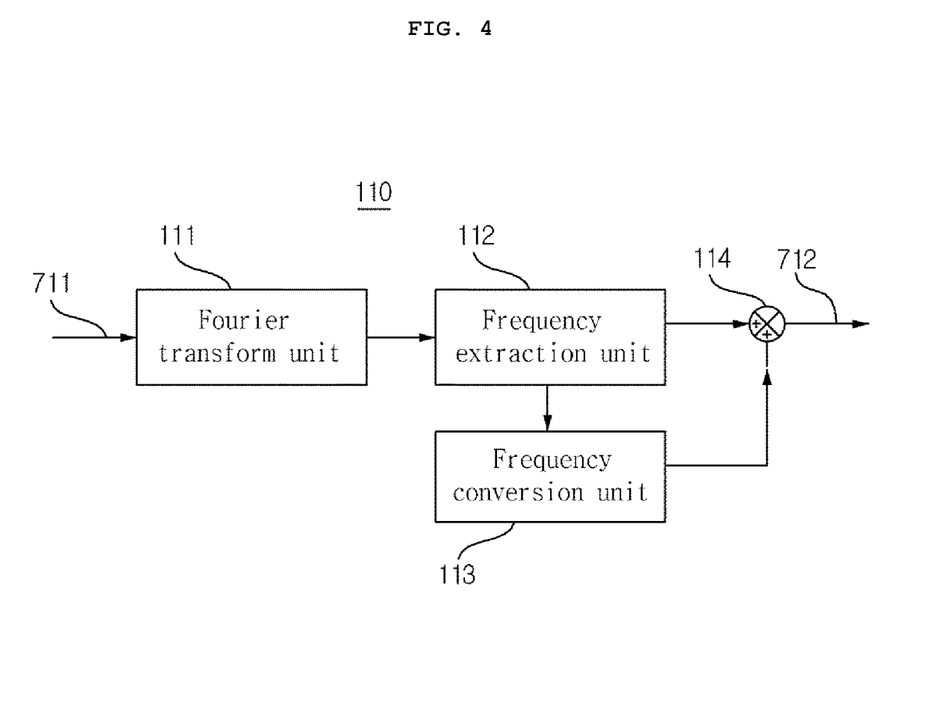
FIG. 4 is a detailed block diagram of a frequency shift unit in accordance with an embodiment of the present invention.

A detailed block diagram of the function of the frequency shift unit 110 is shown in FIG. 4.

Referring to FIG. 4, the frequency shift unit 110 according to an embodiment of the present invention includes a Fourier transform unit 111 configured to obtain frequency components by performing Fourier transform on the input first audio sound source signal 711, a frequency extraction unit 112 configured to extract a specific frequency band from the frequency components obtained by the Fourier transform unit 111, a frequency conversion unit 113 configured to shift the frequency components of the specific frequency band by a predetermined frequency quantity, and a mixing unit 114 configured to output the addition of a frequency component from which the specific frequency band of the first audio sound source signal 711 has been removed by the frequency extraction unit 112 and a frequency band shifted by the frequency conversion unit 113 as the second audio sound source signal 712. The frequency shift unit 110 may be implemented using a DSP as described above. The frequency shift unit 110 of FIG. 4 is only an embodiment in terms of the function of the frequency shift unit 110, and those skilled in the art may modify the frequency shift unit 110 in various forms in order to implement a frequency shift function.

The audio output unit 300 is an element connected to the frequency shift unit 110 and configured to output the first audio output signal 721 and the second audio output signal 722 corresponding to the first audio sound source signal 711 and the second audio sound source signal 712, respectively. The audio output unit 300 may be implemented into an audio amplification stage for driving a headphone or earphone connected to the audio output unit 300. The audio output unit 300 may be implemented in various forms which are known in the art.

The mono conversion unit 120 is an element configured to generate a mono sound source from an audio signal selected from an external audio signal and audio data stored in the sound source storage unit 740 of the audio apparatus for inducing a brainwave in accordance with an embodiment of the present invention. The mono sound source may be a sound source component on one side which is selected from the left and right components of an audio component formed of stereo, or a single mono sound source may be generated by mixing the stereo components. The mono sound source generated by the mono conversion unit 120 is inputted to the frequency shift unit 110 as the first audio sound source signal 711. Furthermore, the mono conversion unit 120 may be configured separately from the frequency shift unit 110 or may be included in the frequency shift unit 110 implemented using a DSP.

The ADC 730 functions to convert an analog signal into a digital signal if the external sound source 710 is the analog signal. As described above, the frequency shift unit 110 may be implemented using a DSP. In this case, the first audio sound source signal 711 inputted to the frequency shift unit 110 needs to be a digital signal. Accordingly, unlike in the case where a signal is stored in the sound source storage unit 740 in a digital form, there is a need for the ADC 730 for converting the external sound source 710, received as an analog signal from the outside, into a digital signal before the analog signal is inputted to the frequency shift unit 110.

The audio apparatus for inducing a brainwave in accordance with an embodiment of the present invention may further include the brainwave sensor 400 for detecting the brainwave state of a user and the heartbeat sensor 500 for detecting the heart rate of the user. The brainwave sensor 400 may be implemented in a hair band form so that it can come in contact with a head portion of a user or may be included in a headphone as a separate element. The heartbeat sensor 500 may be implemented in a wrist band form so that it can be attached to a wrist portion of a user in order to check the heart rate of the user or may be implemented in the form of a common electrode attached to a chest portion. The brainwave sensor 400 and the heartbeat sensor 500 may provide the control unit 200 with information about the current brainwave state and heart rate of a user so that the control unit 200 may determine brainwave induction sequence and speed of audio that is played back based on the current brainwave or heart beat state of the user.

A step for inducing the current brainwave state of a user, sensed by the brainwave sensor, to a target brainwave state set by the user may be performed in accordance with a step for sequentially increasing the frequency of a brainwave (e.g., delta wave-theta wave-alpha wave-beta wave) or decreasing the brainwave (e.g., beta wave-alpha wave-theta wave-delta wave). Alternatively, the frequency of a brainwave induced based on the frequency may be sequentially decreased like 30-25-20-15-10-5 Hz or may be increased in opposite order. The current brainwave state may be naturally moved to the target brainwave state by such an induction.

For example, if a user wants to induce a change of his or her brainwave from a current brainwave state to a delta wave state (sleep state) when the current brainwave state is a beta wave state (daily life state), the control unit 200 does not control the frequency shift unit 110 so that the current brainwave state is directly changed to the delta wave state, but may control the frequency shift unit 110 so that the current brainwave state is changed to the delta wave state through the beta wave-alpha wave (stable state)-theta wave (doziness state). In contrast, if a user wants to induce a change of his or her brain from a current brainwave state to the beta wave state when the current brainwave state is the theta wave state, the control unit 200 may control the frequency shift unit 110 so that the current brainwave state is changed to the beta wave state through the theta wave-alpha wave. Furthermore, if a user is stabilized and thus a current heart rate is slow, the playback of audio may become slow in order to help a change from the brainwave state of the user to the delta wave state.

The control unit 200 controls the frequency shift unit 110 in response to a user's manipulation or predetermined setting so that a frequency band and specific frequency quantity to be shifted from the first audio sound source signal 711 is set or varied. Furthermore, as described above, the control unit 200 may control the induction sequence of a brainwave or playback speed of the first and the second audio sound source signals 711 and 712 in order to reach a brainwave state requested by a user based on information about the current brainwave state and heart rate of the user sensed by the brainwave sensor 400 and the heartbeat sensor 500.

The audio apparatus for inducing a brainwave in accordance with an embodiment of the present invention may further include the sound source selection unit 750 capable of selecting one of the external sound source 710 and sound source data stored in the sound source storage unit 740, that is, a source for the first audio sound source signal 711 inputted to the frequency shift unit 110. A sound source signal selected by the sound source selection unit 750 is inputted to the frequency shift unit 110 through the mono conversion unit 120 as the first audio sound source signal 711.

Furthermore, the audio apparatus for inducing a brainwave in accordance with an embodiment of the present invention includes a user interface 600 for receiving a manipulation command from a user or displaying the operating state of the audio apparatus for inducing a brainwave.

The user interface 600 may be implemented using a known keypad and display means, and a detailed description thereof is omitted.

Figure 6:
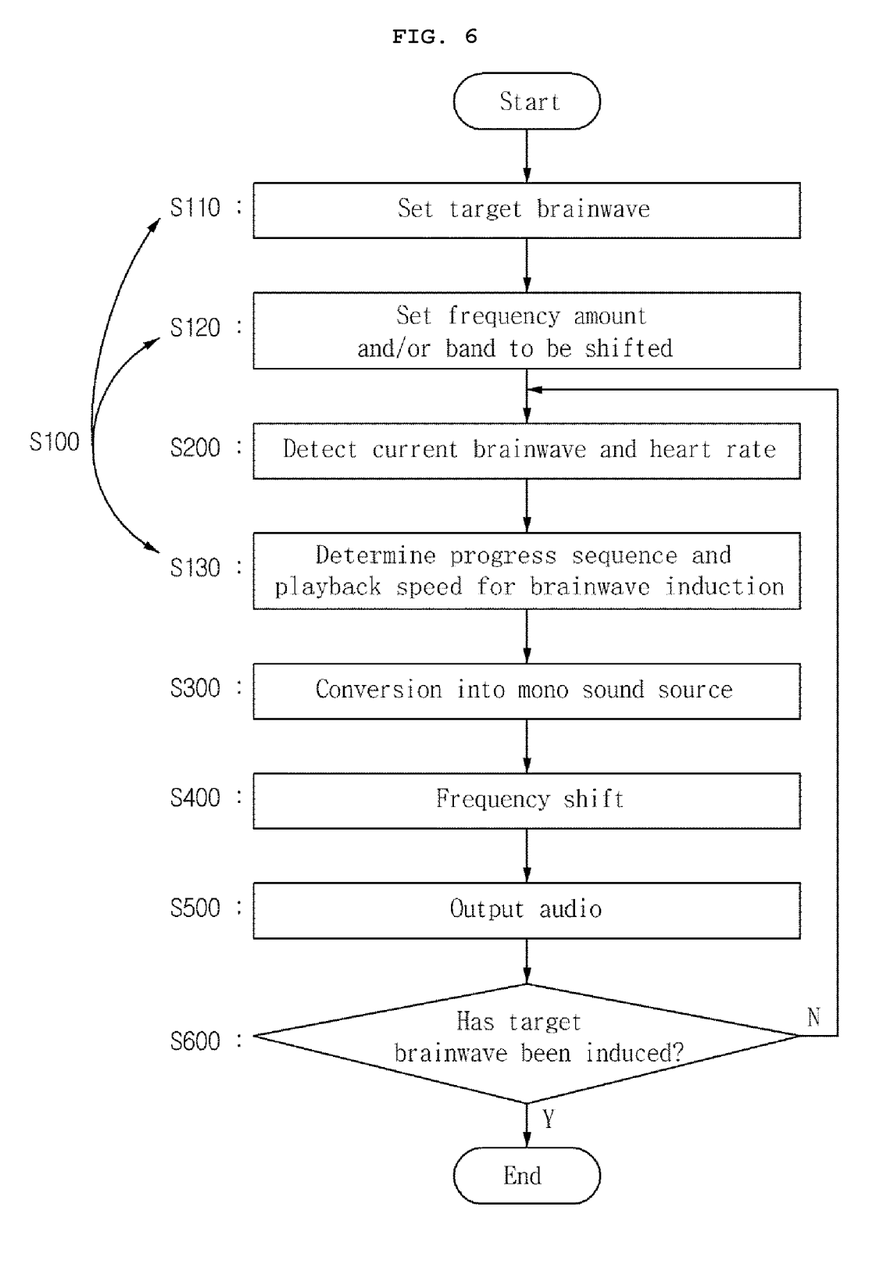
FIG. 6 is a flowchart illustrating a method for inducing a brainwave using a binaural beat in accordance with an embodiment of the present invention.

FIG. 6 is a flowchart illustrating a method for inducing a brainwave using a binaural beat in accordance with an embodiment of the present invention.

Referring to the flowchart of FIG. 6, the method for inducing a brainwave using a binaural beat in accordance with an embodiment of the present invention includes a control step S100 for changing at least one of a frequency band to be shifted or a specific frequency in response to a user's manipulation or predetermined setting, a frequency shift step S400 for receiving the first audio sound source signal 711 and generating the second audio sound source signal 712 by shifting the frequency band of the first audio sound source signal 711 by the frequency quantity, and an audio output step S500 for outputting the first audio output signal 721 and the second audio output signal 722 corresponding to the first audio sound source signal 711 and the second audio sound source signal 712, respectively.

The control step S100 includes a step S110 for setting a target brainwave to be induced in response to user setting and a step S120 for setting the frequency quantity to be shifted and/or the frequency band to be shifted so that the target brainwave is induced. Furthermore, if the method for inducing a brainwave in accordance with an embodiment of the present invention further includes a sensing step S200 for detecting the brainwave state and heart rate of the user, the control step S100 may include a step S130 for setting a progress sequence so that brainwaves are sequentially induced in response to a brainwave state of the user or for changing playback speed of the first and the second audio sound source signals 711 and 712 in response to the heart rate of the user. The effects of the step S130 have been described above, and a description thereof is omitted.

The method for inducing a brainwave in accordance with an embodiment of the present invention may further include a mono sound source conversion step S300 for generating the first audio sound source signal 711 by converting an external audio signal or audio data stored in the sound source storage unit 740 into a mono sound source. The mono sound source may be generated by selecting one of the left and right sides of a stereo component of the audio signal or audio data or may be generated by mixing the stereo components. The frequency of the mono sound source generated in the mono sound source conversion step is shifted in the frequency shift step S400.

The method for inducing a brainwave in accordance with an embodiment of the present invention may further include a step S600 for determining whether the current brainwave state of the user has reached the target brainwave state. If, as a result of the determination, it is determined that the current brainwave state has not yet reached the target brainwave state, audio continues to be played back based on a proper induction sequence and playback speed of a brainwave. If, as a result of the determination, it is determined that the current brainwave state has reached the target brainwave state, the audio apparatus for inducing a brainwave in accordance with an embodiment of the present invention stops the playback of audio according to a frequency shift and stops operating.

Figure 7:
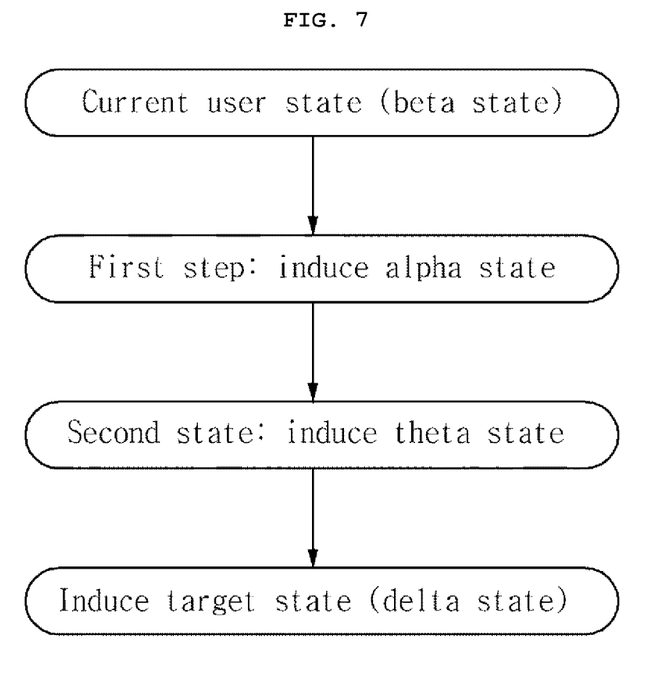
FIG. 7 is a flowchart illustrating a step for inducing a brainwave in accordance with an embodiment of the present invention.

FIG. 7 illustrates a process for inducing a brainwave using the audio apparatus for inducing a brainwave in accordance with an embodiment of the present invention.

If the current brainwave state of the user is detected to be the beta wave state (daily life state) in the sensing step S200 for detecting the brainwave state and heart rate of the user and the user has sets his or her brainwave so that it is changed from the current brainwave state to the delta wave state (sleep state) in the step S110 for setting the target brainwave, the control step S100 does not control the frequency shift step S400 so that the current brainwave state is directly changed to the delta wave state, but may control the frequency shift step S400 so that the current brainwave state is changed to the delta wave state via the alpha wave (stable state)-theta wave (doziness state), as shown in FIG. 7.

The audio apparatus and method for inducing a brainwave using a binaural beat in accordance with the embodiments of the present invention have an advantage in that a user can hear a music signal or an audio signal for learning without being aware of the distortion of a sound source and can change his or her brainwave state without resistance or monotonousness because a required brainwave state is changed by applying a binaural beat to a specific frequency band of an audio signal, in particular, a music signal.

Furthermore, the audio apparatus and method for inducing a brainwave using a binaural beat in accordance with the embodiments of the present invention have an advantage in that a current brainwave state of a user can be changed to a target brainwave state naturally and efficiently because the current brainwave state is taken into consideration and changed to the target brainwave state stepwise.

Although the present invention has been described in connection with the embodiments based on the description and drawings, the embodiments are only illustrative. Those skilled in the art to which the present invention pertains may understand that various other modifications and equivalent embodiments are possible. Accordingly, the true scope of the present invention should be determined by the technical spirit of the following claims.

What is claimed is:

1. An audio apparatus for inducing a brainwave using a binaural beat, the audio apparatus comprising:
   a frequency shift unit configured to receive a first audio sound source signal and to generate a second audio sound source signal by shifting a portion of a frequency band of the first audio sound source signal by a specific frequency;
   an audio output unit connected to the frequency shift unit and configured to output a first audio output signal and a second audio output signal corresponding to the first audio sound source signal and the second audio sound source signal, respectively; and
   a control unit configured to change at least one of the portion of the frequency band and the specific frequency based on to a user's manipulation or predetermined setting,
   wherein the control unit differently sets a lowest limit of the portion of the frequency band of the first audio sound source signal for each of a plurality of target brainwave states, and
   wherein the frequency shift unit generates the second audio sound source signal by shifting the portion of the frequency band above the lowest limit by the specific frequency.

2. The audio apparatus of claim 1, further comprising a mono conversion unit configured to generate the first audio sound source signal from an external audio signal or audio data stored in the audio apparatus as a mono sound source,
   wherein the mono sound source comprises a sound source on one side which is selected from stereo components of the audio signal or audio data or a sound source generated by mixing the stereo components.

3. The audio apparatus of claim 2, further comprising an analog-digital converter configured to convert the external audio signal into a digital signal.

4. The audio apparatus of claim 1, wherein:
the portion of the frequency band is selected from a frequency band of 500 to 6000 Hz; and
the specific frequency comprises a frequency within any one of frequency ranges of an alpha wave, a beta wave, a theta wave, and a delta wave which are brainwaves to be induced.

5. The audio apparatus of claim 4, wherein the control unit sets one of the plurality of target brainwave states based on a user setting.

6. The audio apparatus of claim 5, further comprising:
a brainwave sensor attached to a head of the user and configured to detect a current brainwave state; and
a heartbeat sensor configured to detect a heart rate of the user,
wherein the control unit controls the frequency shift unit to sequentially induce the target brainwave state based on the current brainwave state and the control unit changes a playback speed of the first and the second audio sound source signals based on the heart rate.

7. The audio apparatus of claim 6, wherein the control unit controls the frequency shift unit to set an induction sequence from the current brainwave state detected by the brainwave sensor to the target brainwave state, the induction sequence being set to be a state in which a frequency of the brainwave is sequentially decreased or a state in which the frequency of the brainwave is sequentially increased.

8. The audio apparatus of claim 1, further comprising a headphone configured to convert the first and the second audio output signals into first and second sounds, respectively, and output the first and second sounds,
wherein the first sound corresponding to the first audio output signal is output to a first side of the headphone, and the second sound corresponding to the second audio output signal is output to a second side of the headphone.

9. A method for inducing a brainwave using a binaural beat, the method comprising:
a frequency shift step of receiving a first audio sound source signal and generating a second audio sound source signal by shifting a portion of a frequency band of the first audio sound source signal by a specific frequency, the frequency shift step being performed by a frequency shift unit;
an audio output step of outputting a first audio output signal and a second audio output signal corresponding to the first audio sound source signal and the second audio sound source signal, respectively, the audio output step being performed by an audio output unit; and
a control step of changing at least one of the portion of the frequency band and the specific frequency based on a user's manipulation or predetermined setting, the control step being performed by a control unit,
wherein, in the control step, the control unit differently sets a lowest limit of the portion of the frequency band of the first audio sound source signal for each of a plurality of target brainwave states, and
wherein, in the frequency shift step, the frequency shift unit generates the second audio sound source signal by shifting the portion of the frequency band above the lowest limit by the specific frequency.

10. The method of claim 9, further comprising a mono sound source conversion step of generating the first audio sound source signal from an external audio signal or audio data stored in a sound source storage unit as a mono sound source, the mono sound source conversion step being performed by a mono conversion unit,
wherein the mono sound source comprises a sound source on one side which is selected from stereo components of the audio signal or audio data or a sound source generated by mixing the stereo components.

11. The method of claim 9, wherein:
the portion of the frequency band is selected from a frequency band of 500 to 6000 Hz; and
the specific frequency comprises a frequency within any one of frequency ranges of an alpha wave, a beta wave, a theta wave, and a delta wave which are brainwaves to be induced.

12. The method of claim 11, wherein the control step comprises a setting step of setting one of the plurality of target brainwave state based on a user setting.

13. The method of claim 12, further comprising:
a brainwave sensing step of detecting a current brainwave state of the user, the brainwave sensing step being performed by a brainwave sensor; and
a heartbeat sensing step of detecting a heart rate of the user, the heartbeat sensing step being performed by a heartbeat sensor,
wherein the control step further comprises:
sequentially inducing the target brainwave state based on the current brainwave state; and
changing a playback speed of the first and the second audio sound source signals based on the heart rate.

14. The method of claim 13, wherein the control unit controls the frequency shift unit to set an induction sequence from the current brainwave state detected in the brainwave sensing step to the target brainwave state, the induction sequence being set to be a state in which a frequency of the brainwave is sequentially decreased or a state in which the frequency of the brainwave is sequentially increased.

* * * * *